United States Patent
Kallenberger

(10) Patent No.: US 11,944,340 B2
(45) Date of Patent: Apr. 2, 2024

(54) SUCTION AND IRRIGATION VALVE AND METHOD OF PRIMING SAME IN A ROBOTIC SURGICAL SYSTEM

(71) Applicant: Cilag GmbH International, Zug (CH)

(72) Inventor: Kris E. Kallenberger, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 166 days.

(21) Appl. No.: 17/345,119

(22) Filed: Jun. 11, 2021

(65) Prior Publication Data

US 2022/0395290 A1 Dec. 15, 2022

(51) Int. Cl.
*A61B 34/37* (2016.01)
*A61B 17/32* (2006.01)

(52) U.S. Cl.
CPC ...... *A61B 17/320068* (2013.01); *A61B 34/37* (2016.02); *A61B 2017/32007* (2017.08); *A61B 2017/320095* (2017.08); *A61B 2017/320097* (2017.08); *A61B 2217/007* (2013.01)

(58) Field of Classification Search
CPC .. A61B 17/320068; A61B 2017/32007; A61B 2017/320095; A61B 2017/320097; A61B 34/37; A61B 2217/007
See application file for complete search history.

(56) References Cited

U.S. PATENT DOCUMENTS

| | | | |
|---|---|---|---|
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 8,210,411 B2 | 7/2012 | Yates et al. | |
| 8,408,439 B2 | 4/2013 | Huang et al. | |
| 8,453,914 B2 | 6/2013 | Laurent et al. | |
| 8,663,220 B2 | 3/2014 | Wiener et al. | |
| 9,186,142 B2 | 11/2015 | Fanelli et al. | |
| 9,517,065 B2 | 12/2016 | Simms et al. | |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |

(Continued)

OTHER PUBLICATIONS

U.S. Non-Provisional U.S. Appl. No. 17/076,956, entitled "Surgical Instrument with an Articulatable Shaft Assembly and Dual End Effector Role," filed Oct. 22, 2020.

(Continued)

*Primary Examiner* — Ashley L Fishback
(74) *Attorney, Agent, or Firm* — Frost Brown Todd LLP

(57) ABSTRACT

A method of priming a surgical instrument, wherein the surgical instrument includes a shaft assembly including a lumen, and a valve assembly. The valve assembly includes a first inlet configured to receive the fluid from a fluid source, a second inlet configured to receive a suction from a vacuum source, an outlet in fluid communication with the lumen, a valve chamber, and at least one valve plug. The method includes activating the fluid source to provide the fluid to the first inlet, activating the vacuum source to provide the suction to the second inlet, transitioning the at least one valve plug from a first position to a second position, and transferring a first portion of the fluid from the first inlet toward the vacuum source through the second inlet thereby priming the surgical instrument.

16 Claims, 10 Drawing Sheets

(56) References Cited

U.S. PATENT DOCUMENTS

| | | | |
|---|---|---|---|
| 9,949,785 B2 | 4/2018 | Price et al. | |
| 10,092,292 B2 | 10/2018 | Boudreaux et al. | |
| 2006/0079874 A1 | 4/2006 | Faller et al. | |
| 2007/0191713 A1 | 8/2007 | Eichmann et al. | |
| 2008/0200940 A1 | 8/2008 | Eichmann et al. | |
| 2009/0099520 A1 | 4/2009 | Millman et al. | |
| 2009/0294359 A1* | 12/2009 | Hopping | A61M 1/288 210/141 |
| 2014/0358155 A1* | 12/2014 | DeBoer | A61F 2/1662 606/107 |
| 2017/0105752 A1 | 4/2017 | Boudreaux et al. | |
| 2019/0282401 A1 | 9/2019 | Sorensen et al. | |
| 2021/0393340 A1 | 12/2021 | Beckman et al. | |
| 2022/0313291 A1* | 10/2022 | Nakano | A61B 17/22 |

OTHER PUBLICATIONS

U.S. Non-Provisional U.S. Appl. No. 17/076,959, entitled "Ultrasonic Surgical Instrument with a Distally Grounded Acoustic Wave," filed Oct. 22, 2020.

U.S. Non-Provisional U.S. Appl. No. 17/077,067, entitled "Surgical Instrument and Carrier Kart Supporting Ultrasonic Transducer," filed Oct. 22, 2020.

U.S. Non-Provisional U.S. Appl. No. 17/077,086, entitled "Carrier Kart and Jaw Closure of an Ultrasonic Surgical Instrument," filed Oct. 22, 2020.

U.S. Non-Provisional U.S. Appl. No. 17/077,098, entitled "Ultrasonic Surgical Instrument with a Multiplanar Articulation Joint," filed Oct. 22, 2020.

U.S. Non-Provisional U.S. Appl. No. 17/077,110, entitled "Ultrasonic Surgical Instrument with a Mid-Shaft Closure System and Related Methods," filed Oct. 22, 2020.

U.S. Non-Provisional U.S. Appl. No. 17/077,130, entitled "Surgical Instrument with Clamping Sensor Feedback and Related Methods," filed Oct. 22, 2020.

U.S. Non-Provisional U.S. Appl. No. 17/077,136, entitled "Surgical Instrument with Non-Clamping Sensor Feedback and Related Methods," filed Oct. 22, 2020.

U.S. Non-Provisional U.S. Appl. No. 17/077,139, entitled "Ultrasonic Surgical Instrument with a Fixed Transducer Grounding," filed Oct. 22, 2020.

U.S. Non-Provisional U.S. Appl. No. 17/077,146, entitled "Ultrasonic Surgical Instrument with a Shaft Assembly and Elongated Waveguide Support Arrangement," filed Oct. 22, 2020.

U.S. Non-Provisional U.S. Appl. No. 17/077,152, entitled "Damping Rings for an Ultrasonic Surgical Instrument," filed Oct. 22, 2020.

U.S. Non-Provisional U.S. Appl. No. 17/077,250, entitled "Ultrasonic Surgical Instrument with a Carrier Kart and Reusable Stage," filed Oct. 22, 2020.

U.S. Non-Provisional U.S. Appl. No. 17/077,373, entitled "Surgical Instrument with a Carrier Kart and Various Communication Cable Arrangements," filed Oct. 22, 2020.

U.S. Non-Provisional U.S. Appl. No. 17/345,617, entitled "Suction and Irrigation Valve for a Robotic Surgical System and Related Matters," filed Jun. 11, 2021.

International Search Report and Written Opinion dated Sep. 13, 2022 for Application No. PCT/IB2022/055405, 20 pgs.

\* cited by examiner

SUCTION AND IRRIGATION VALVE AND METHOD OF PRIMING SAME IN A ROBOTIC SURGICAL SYSTEM

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically assisted surgery. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletol gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a surgical stapler, a tissue grasper, a needle driver, an electrosurgical cautery probes, etc. Each of these structures performs functions for the surgeon, for example, cutting tissue, coagulating tissue, holding or driving a needle, grasping a blood vessel, dissecting tissue, or cauterizing tissue.

Examples of surgical instruments include suction-irrigation devices. Suction-irrigation devices are configured to apply at least one of suction or irrigation to the surgical site, such as for flushing of fluid and debris at the surgical site via irrigation and for removal of fluid and debris from the surgical site via suction. In this respect the suction-irrigation devices are configured to connect to a vacuum source for suction and a fluid source for irrigation, although such sources may be stored locally within the suction-irrigation device. While irrigation may be directed to the surgical site separately from suction, in some examples irrigation may occur simultaneously with suction. Moreover, during procedures, the medical operator may select the suction or irrigation as desired. Examples of suction-irrigation devices may simply perform suction and irrigation or be incorporated into other surgical instruments for added functionality.

Additional examples of other surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers and associated features are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued on Nov. 17, 2015; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 10,092,292, entitled "Staple Forming Features for Surgical Stapling Instrument," issued Oct. 9, 2018; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; and U.S. Pat. No. 8,210,411, entitled "Motor-Driven Surgical Instrument," issued Jul. 3, 2012. The disclosure of each of the above-cited U.S. patents is incorporated by reference herein in its entirety.

Still additional examples of such other surgical instruments include an ultrasonic surgical instrument with end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element. Examples of ultrasonic surgical instruments and related concepts are disclosed in U.S. Pub. No. 2006/0079874, entitled "Tissue Pad for Use with an Ultrasonic Surgical Instrument," published Apr. 13, 2006, now abandoned; U.S. Pub. No. 2007/0191713, entitled "Ultrasonic Device for Cutting and Coagulating," published Aug. 16, 2007, now abandoned; U.S. Pub. No. 2008/0200940, entitled "Ultrasonic Device for Cutting and Coagulating," published Aug. 21, 2008, now abandoned, U.S. Pat. No. 9,949,785, entitled "Ultrasonic Surgical Instrument with Electrosurgical Feature," issued Apr. 24, 2018; and U.S. Pat. No. 8,663,220, entitled "Ultrasonic Surgical Instruments," issued Mar. 4, 2014. The disclosure of each of the above-cited U.S. patent Publications and U.S. patents is incorporated by reference herein in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
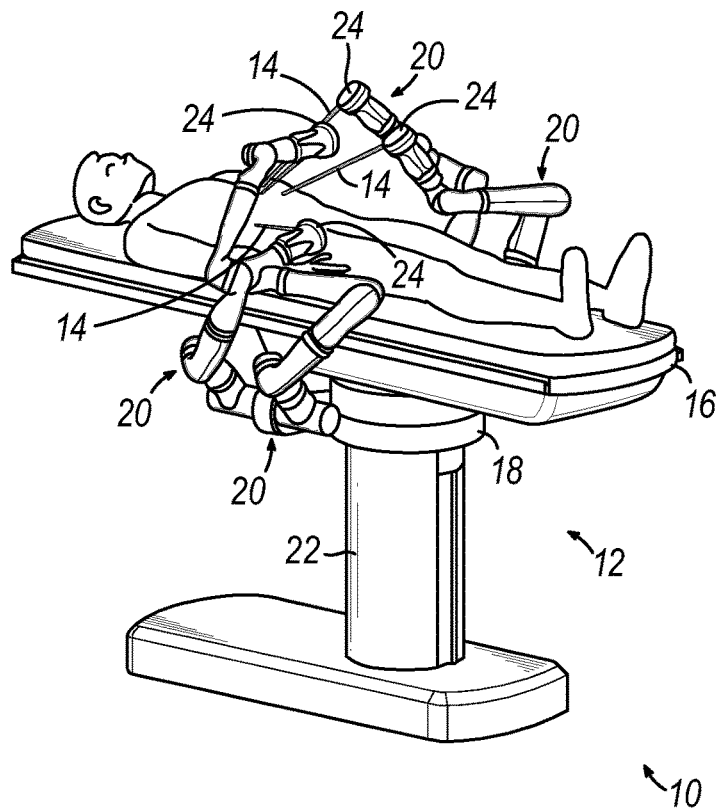
FIG. 1 depicts a perspective view of a first example of a table-based robotic system configured for a laparoscopic procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "clockwise," "counterclockwise," "longitudinal," "inner," "outer," and "upper," also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

In addition to performing the breadth of procedures, the robotically-enabled medical system may provide additional benefits, such as enhanced imaging and guidance to assist the medical professional. Additionally, the robotically-enabled medical system may provide the medical professional with the ability to perform the procedure from an ergonomic position without the need for awkward arm motions and positions. Still further, the robotically-enabled medical system may provide the medical professional with the ability to perform the procedure with improved ease of use such that one or more of the instruments of the robotically-enabled medical system may be controlled by a single operator.

I. Exemplary Robotically-Enabled Medical System

FIG. 1 shows an exemplary robotically-enabled medical system, including a first example of a table-based robotic system (10). Table-based robotic system (10) of the present example includes a table system (12) operatively connected to a surgical instrument (14) for a diagnostic and/or therapeutic procedure in the course of treating a patient. Such procedures may include, but are not limited, to bronchoscopy, ureteroscopy, a vascular procedure, and a laparoscopic procedure. To this end, surgical instrument (14) is configured for a laparoscopic procedure, although it will be appreciated that any instrument for treating a patient may be similarly used. At least part of table-based robotic system (10) may be constructed and operable in accordance with at least some of the teachings of any of the various patents, patent application publications, and patent applications that are cited herein.

A. First Exemplary Table-Based Robotic System

With respect to FIG. 1, table-based robotic system (10) includes table system (12) having a platform, such as a table (16), with a plurality of carriages (18) which may also be referred to herein as "arm supports," respectively supporting the deployment of a plurality of robotic arms (20). Table-based robotic system (10) further includes a support structure, such as a column (22), for supporting table (16) over the floor. Table (16) may also be configured to tilt to a desired angle during use, such as during laparoscopic procedures. Each robotic arm (20) includes an instrument driver (24) configured to removably connect to and manipulate surgical instrument (14) for use. In alternative examples, instrument drivers (24) may be collectively positioned in a linear arrangement to support the instrument extending therebetween along a "virtual rail" that may be repositioned in space by manipulating the one or more robotic arms (20) into one or more angles and/or positions. In practice, a C-arm (not shown) may be positioned over the patient for providing fluoroscopic imaging.

In the present example, column (22) includes carriages (18) arranged in a ring-shaped form to respectively support one or more robotic arms (20) for use. Carriages (18) may translate along column (22) and/or rotate about column (22) as driven by a mechanical motor (not shown) positioned within column (22) in order to provide robotic arms (20) with access to multiples sides of table (16), such as, for example, both sides of the patient. Rotation and translation of carriages (18) allows for alignment of instruments, such as surgical instrument (14) into different access points on the patient. In alternative examples, such as those discussed below in greater detail, table-based robotic system (10) may include a patient table or bed with adjustable arm supports including a bar (26) (see FIG. 2) extending alongside. One or more robotic arms (20) (e.g., via a shoulder with an elbow joint) may be attached to carriages (18), which are vertically adjustable so as to be stowed compactly beneath the patient table or bed, and subsequently raised during use.

Table-based robotic system (10) may also include a tower (not shown) that divides the functionality of table-based robotic system (10) between table (16) and the tower to reduce the form factor and bulk of table (16). To this end, the tower may provide a variety of support functionalities to table (16), such as processing, computing, and control capabilities, power, fluidics, and/or optical and sensor processing. The tower may also be movable so as to be positioned away from the patient to improve medical professional access and de-clutter the operating room. The tower may also include a master controller or console that provides both a user interface for operator input, such as keyboard and/or pendant, as well as a display screen, including a touchscreen, for pre-operative and intra-operative information, including, but not limited to, real-time imaging, navigation, and tracking information. In one example, the tower may include gas tanks to be used for insufflation.

B. Second Exemplary Table-Based Robotic System

Figure 2:
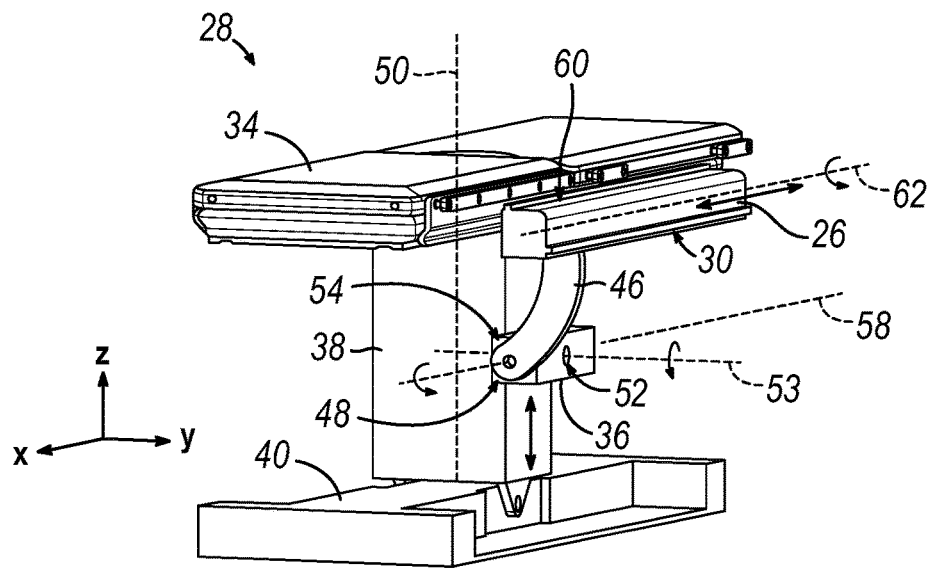
FIG. 2 depicts a perspective view of a second example of a table-based robotic system.
Figure 3:
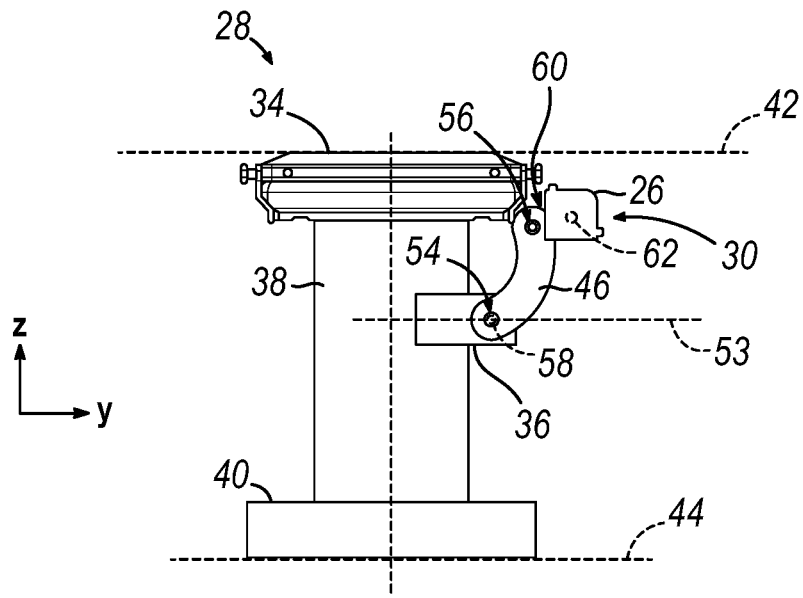
FIG. 3 depicts an end elevational view of the table-based robotic system of FIG. 2.
Figure 4:
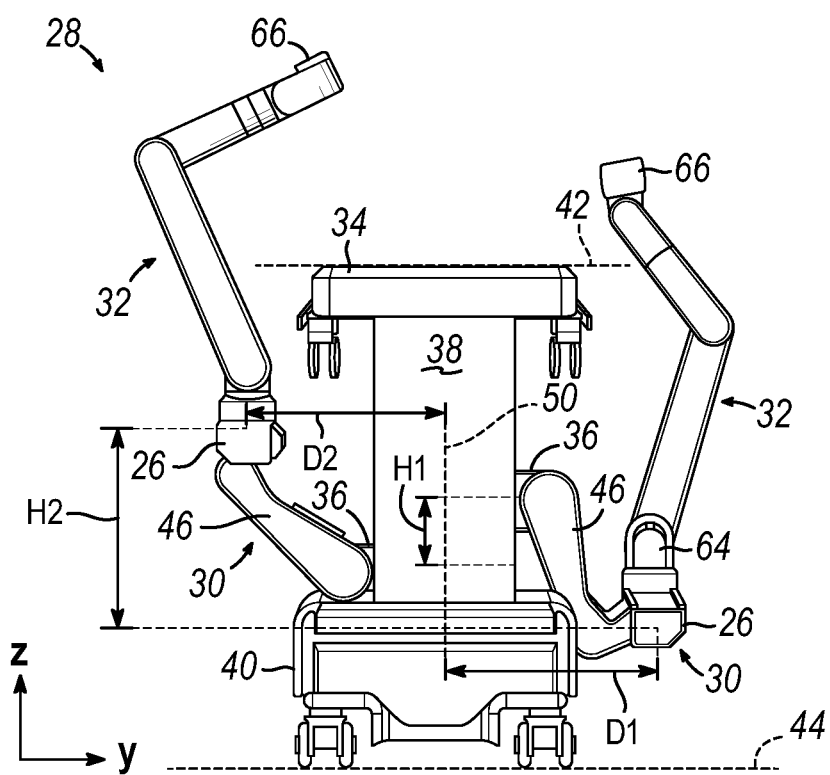
FIG. 4 depicts the end elevational view of the table-based robotic system of FIG. 3 including a pair of exemplary robotic arms.

As discussed briefly above, a second exemplary table-based robotic system (28) includes one or more adjustable arm supports (30) including bars (26) configured to support one or more robotic arms (32) relative to a table (34) as shown in FIGS. 2-4. In the present example, a single and a pair of adjustable arm supports (30) are shown, though additional arm supports (30) may be provided about table (34). Adjustable arm support (30) is configured to selectively move relative to table (34) so as to alter the position of adjustable arm support (30) and/or any robotic arms (32) mounted thereto relative to table (34) as desired. Such adjustable arm supports (30) provide high versatility to table-based robotic system (28), including the ability to easily stow one or more adjustable arm supports (30) with robotic arms (32) beneath table (34).

Each adjustable arm support (30) provides several degrees of freedom, including lift, lateral translation, tilt, etc. In the present example shown in FIGS. 2-4, arm support (30) is configured with four degrees of freedom, which are illustrated with arrows. A first degree of freedom allows adjustable arm support (30) to move in the z-direction ("Z-lift"). For example, adjustable arm support (30) includes a vertical carriage (36) configured to move up or down along or relative to a column (38) and a base (40) supporting table (34). A second degree of freedom allows adjustable arm support (30) to tilt about an axis extending in the y-direction. For example, adjustable arm support (30) includes a rotary joint, which allows adjustable arm support (30) to align the bed in a Trendelenburg position. A third degree of freedom allows adjustable arm support (30) to "pivot up" about an axis extending in the x-direction, which may be useful to adjust a distance between a side of table (34) and adjustable arm support (30). A fourth degree of freedom allows translation of adjustable arm support (30) along a longitudinal length of table (34), which extends along the x-direction. Base (40) and column (38) support table (34) relative to a support surface, which is shown along a support axis (42) above a floor axis (44) and in the present example. While the present example shows adjustable arm support (30) mounted to column (38), arm support (30) may alternatively be mounted to table (34) or base (40).

As shown in the present example, adjustable arm support (30) includes vertical carriage (36), a bar connector (46), and bar (26). To this end, vertical carriage (36) attaches to column (38) by a first joint (48), which allows vertical carriage (36) to move relative to column (38) (e.g., such as up and down a first, vertical axis (50) extending in the z-direction). First joint (48) provides the first degree of freedom ("Z-lift") to adjustable arm support (30). Adjustable arm support (30) further includes a second joint (52), which provides the second degree of freedom (tilt) for adjustable arm support (30) to pivot about a second axis (53) extending in the y-direction. Adjustable arm support (30) also includes a third joint (54), which provides the third degree of freedom ("pivot up") for adjustable arm support (30) about a third axis (58) extending in the x-direction. Furthermore, an additional joint (56) mechanically constrains third joint (54) to maintain a desired orientation of bar (26) as bar connector (46) rotates about third axis (58). Adjustable arm support (30) includes a fourth joint (60) to provide a fourth degree of freedom (translation) for adjustable arm support (30) along a fourth axis (62) extending in the x-direction.

With respect to FIG. 4, table-based robotic system (28) is shown with two adjustable arm supports (30) mounted on opposite sides of table (34). A first robotic arm (32) is attached to one such bar (26) of first adjustable arm support (30). First robotic arm (32) includes a base (64) attached to bar (26). Similarly, second robotic arm (32) includes base (64) attached to other bar (26). Distal ends of first and second robotic arms (32) respectively include instrument drivers (66), which are configured to attach to one or more instruments such as those discussed below in greater detail.

In one example, one or more robotic arms (32) has seven or more degrees of freedom. In another example, one or more robotic arms (32) has eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base (64) (1-degree of freedom including translation). In one example, the insertion degree of freedom is provided by robotic arm (32), while in another example, such as surgical instrument (14) (see FIG. 6A), the instrument includes an instrument-based insertion architecture.

Figure 5:
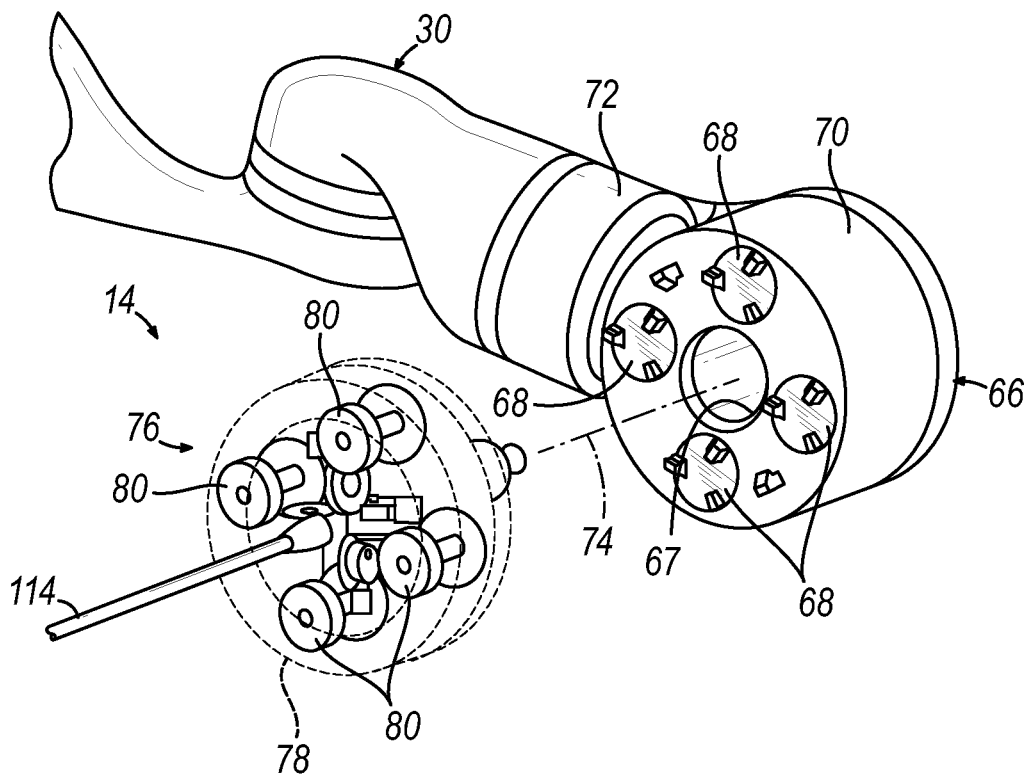
FIG. 5 depicts a partially exploded perspective view of the robotic arm of FIG. 4 having an instrument driver and a first exemplary surgical instrument.

FIG. 5 shows one example of instrument driver (66) in greater detail with surgical instrument (14) removed therefrom. Given the present instrument-based insertion architecture shown with reference to surgical instrument (14), instrument driver (66) further includes a clearance bore (67) extending entirely therethrough so as to movably receive a portion of surgical instrument (14) as discussed below in greater detail. Instrument driver (66) may also be referred to herein as an "instrument drive mechanism," an "instrument device manipulator," or an "advanced device manipulator" (ADM). Instruments may be designed to be detached, removed, and interchanged from instrument driver (66) for individual sterilization or disposal by the medical professional or associated staff. In some scenarios, instrument drivers (66) may be draped for protection and thus may not need to be changed or sterilized.

Each instrument driver (66) operates independently of other instrument drivers (66) and includes a plurality of rotary drive outputs (68), such as four drive outputs (68), also independently driven relative to each other for directing operation of surgical instrument (14). Instrument driver (66) and surgical instrument (14) of the present example are aligned such that the axes of each drive output (68) are parallel to the axis of surgical instrument (14). In use, control circuitry (not shown) receives a control signal, transmits motor signals to desired motors (not shown), compares resulting motor speed as measured by respective encoders (not shown) with desired speeds, and modulates motor signals to generate desired torque at one or more drive outputs (68).

In the present example, instrument driver (66) is circular with respective drive outputs (68) housed in a rotational assembly (70). In response to torque, rotational assembly (70) rotates along a circular bearing (not shown) that connects rotational assembly (70) to a non-rotational portion (72) of instrument driver (66). Power and controls signals may be communicated from non-rotational portion (72) of instrument driver (66) to rotational assembly (70) through electrical contacts therebetween, such as a brushed slip ring connection (not shown). In one example, rotational assembly (70) may be responsive to a separate drive output (not shown) integrated into non-rotatable portion (72), and thus not in parallel to the other drive outputs (68). In any case, rotational assembly (70) allows instrument driver (66) to rotate rotational assembly (70) and drive outputs (68) in conjunction with surgical instrument (14) as a single unit around an instrument driver axis (74).

Any systems described herein, including table-based robotic system (28), may further include an input controller (not shown) for manipulating one or more instruments. In some embodiments, the input controller (not shown) may be coupled (e.g., communicatively, electronically, electrically, wirelessly and/or mechanically) with an instrument such that manipulation of the input controller (not shown) causes a corresponding manipulation of the instrument e.g., via master slave control. In one example, one or more load cells (not shown) may be positioned in the input controller such that portions of the input controller (not shown) are capable of operating under admittance control, thereby advantageously reducing the perceived inertia of the controller while in use.

In addition, any systems described herein, including table-based robotic system (28) may provide for non-radiation-based navigational and localization means to reduce exposure to radiation and reduce the amount of equipment within the operating room. As used herein, the term "localization" may refer to determining and/or monitoring the position of objects in a reference coordinate system. Technologies such as pre-operative mapping, computer vision, real-time electromagnetic sensor (EM) tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

C. Exemplary Surgical Instrument

Figure 6A:
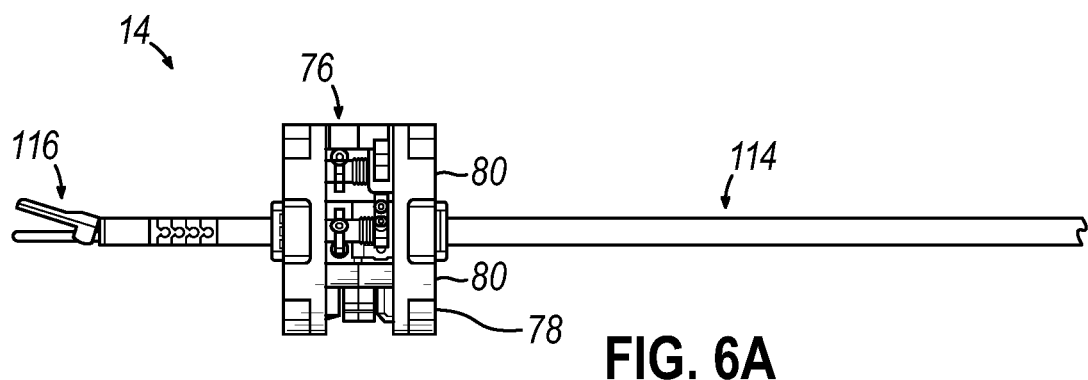
FIG. 6A depicts a side elevational view of the surgical instrument of FIG. 5 in a retracted position.
Figure 6B:
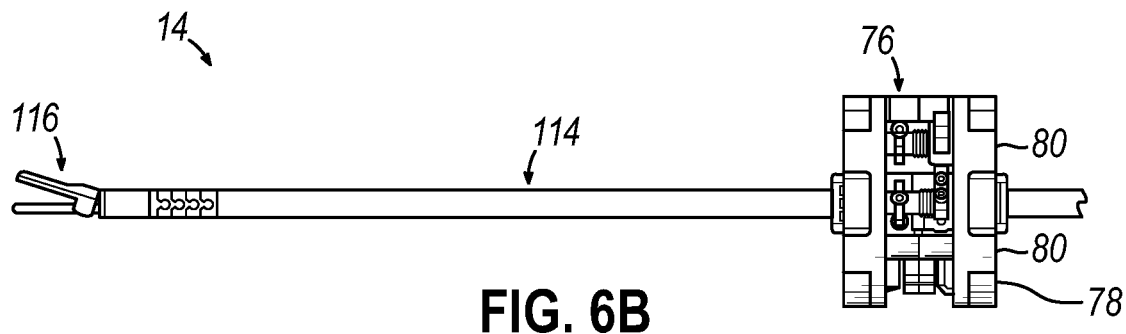
FIG. 6B depicts the side elevational view the surgical instrument similar to FIG. 6A, but in an extended position.

With respect to FIGS. 5-6B and in cooperation with instrument driver (66) discussed above, surgical instrument (14) includes an elongated shaft assembly (114) and an instrument base (76) with an attachment interface (78) having a plurality of drive inputs (80) configured to respectively couple with corresponding drive outputs (68). Shaft assembly (114) of ultrasonic surgical instrument (14) extends from a center of instrument base (76) with an axis substantially parallel to the axes of the drive inputs (80) as discussed briefly above. With shaft assembly (114) positioned at the center of instrument base (76), shaft assembly (114) is coaxial with instrument driver axis (74) when attached and movably received in clearance bore (67). Thus, rotation of rotational assembly (70) causes shaft assembly (114) of surgical instrument (14) to rotate about its own longitudinal axis while clearance bore (67) provides space for translation of shaft assembly (114) during use.

To this end, FIGS. 5-6B show surgical instrument (14) having the instrument-based insertion architecture as discussed briefly above. Surgical instrument (14) includes elongated shaft assembly (114), end effector (116) connected to and extending distally from shaft assembly (114), and instrument base (76) coupled to shaft assembly (114). Notably, insertion of shaft assembly (114) is grounded at instrument base (76) such that end effector (116) is configured to selectively move longitudinally from a retracted position to an extended position, vice versa, and any desired longitudinal position therebetween. As used herein, the retracted position is shown in FIG. 6A and places end effector (116) relatively close and proximally toward instrument base (76), whereas the extended position is shown in FIG. 6B and places end effector (116) relatively far and distally away from instrument base (76). Insertion into and withdrawal of end effector (116) relative to the patient may thus be facilitated by ultrasonic surgical instrument (14), although it will be appreciated that such insertion into and withdrawal may also occur via adjustable arm supports (30) in one or more examples.

While the present example of instrument driver (66) shows drive outputs (68) arranged in rotational assembly (70) so as to face in a distal direction like distally projecting end effector (116) from shaft assembly (114), an alternative instrument driver (not shown) may include drive output (68) arranged on an alternative rotational assembly (70) to face in a proximal direction, opposite of the distally projecting end effector (116). In such an example, surgical instrument (14) may thus have drive inputs (80) facing distally to attach to instrument drivers (66) facing proximally in an opposite direction from that shown in FIG. 5. The invention is thus not intended to be unnecessarily limited to the particular arrangement of drive outputs (68) and drive inputs (80) shown in the present example and any such arrangement for operatively coupling between drive outputs and inputs (68, 80) may be similarly used.

While various features configured to facilitate movement between end effector (116) and drive inputs (80) are described herein, such features may additionally or alternatively include pulleys, cables, carriages, carriers, such as a kinetic articulating rotating tool (KART), and/or other structures configured to communicate movement along shaft assembly (114). Moreover, while instrument base (76) is configured to operatively connect to instrument driver (66) for driving various features of shaft assembly (114) and/or end effector (116) as discussed below in greater detail, it will be appreciated that alternative examples may operatively connect shaft assembly (114) and/or end effector (116) to an alternative handle assembly (not shown). Such handle assembly (not shown) may include a pistol grip (not shown) in one example, configured to be directly gripped and manipulated by the medical professional for driving various features of shaft assembly (114) and/or end effector (116). The invention is thus not intended to be unnecessarily limited to use with instrument driver (66).

II. Exemplary Suction-Irrigation Surgical Instrument

In some instances, it may be desirable to use various alternative surgical instruments with robotic systems (10, 28) described above in addition to, or in lieu of, surgical instrument (14). Such alternative surgical instruments may be desirable to provide improved operability and/or functionality when used with robotic systems (10, 28). For instance, as described above, surgical instrument (14) may move between a retracted position and extended position. Additionally, it may be beneficial to translate a portion of surgical instrument (14) along a support structure to provide increased surgical access without increasing the dimensions of surgical instrument (14). As also described above, use of rotational assembly (70) of robotic arm (20, 32) may enable rotation of the entire surgical instrument (14), rather than specific structures of surgical instrument (14) being rotatable.

One such example of these alternative surgical instruments includes a second exemplary surgical instrument (210), which may also be referred to as surgical stapler (210) and is discussed below in greater detail. Additional examples of alternative surgical instruments and/or associated features for incorporation with robotic systems (10, 28) are described in U.S. patent application Ser. No. 16/946,363, entitled "Articulation Mechanisms for Robotic Surgical Tools," filed on Jun. 18, 2020, published as U.S. Pub. No. 2021/0393340 on Dec. 23, 2021; U.S. patent application Ser. No. 17/077,067, entitled "Surgical Instrument and Carrier KART Supporting Ultrasonic Transducer," filed on Oct. 22, 2020, published as U.S. Pub. No. 2022/0125465 on Apr. 28, 2022; U.S. patent application Ser. No. 17/077,086, entitled "Carrier KART and Jaw Closure of an Ultrasonic Surgical Instrument," filed on Oct. 22, 2020, published as U.S. Pub. No. 2022/0125466 on Apr. 28, 2022; U.S. patent application Ser. No. 17/077,130, entitled "Surgical Instrument with Clamping Sensor Feedback and Related Methods," filed on Oct. 22, 2020, published as U.S. Pub. No. 2022/0125469 on Apr. 28, 2022; U.S. patent application Ser. No. 17/077,136, entitled "Surgical Instrument with Non-clamping Sensor Feedback and Related Methods," filed on Oct. 22, 2020published as U.S. Pub. No. 2022/0125470 on Apr. 28, 2022; U.S. patent application Ser. No. 17/077,250, entitled "Ultrasonic Surgical Instrument with a Carrier KART and Reusable Stage," filed on Oct. 22, 2020, published as U.S. Pub. No. 2022/0125472 on Apr. 28, 2022; U.S. patent application Ser. No. 17/077,373, entitled "Surgical Instrument with a Carrier KART and Various Communication Cable Arrangements," filed on Oct. 22, 2020, published as U.S. Pub. No. 2022/0125473 on Apr. 28, 2022; U.S. patent application Ser. No. 17/077,139, entitled "Ultrasonic Surgical Instrument with a Fixed Transducer Grounding," filed on Oct. 22, 2020, published as U.S. Pub. No. 2022/0125471 on Apr. 28, 2022; U.S. patent application Ser. No. 17/077,146, entitled "Ultrasonic Surgical Instrument with a Shaft Assembly and Elongated Waveguide Support Arrangement," filed on Oct. 22, 2020, published as U.S. Pub. No. 2022/0125460 on Apr. 28, 2022; U.S. patent application Ser. No. 17/077,152, entitled "Damping Rings for an Ultrasonic Surgical Instrument," filed on Oct. 22, 2020, published as U.S. Pat. No. 11,806,037 on Nov. 7, 2023; U.S. U.S. patent application Ser. No. 17/077,110, entitled "Ultrasonic Surgical Instrument with a Mid-shaft Closure System and Related Methods," filed on Oct. 22, 2020, published as U.S. Pub. No. 2022/0125468 on Apr. 28, 2022; U.S. patent application Ser. No. 17/076,956, entitled "Surgical Instrument with an Articulatable Shaft Assembly and Dual End Effector Roll," filed on Oct. 22, 2020, published as U.S. Pub. No. 2022/0125463 on Apr. 28, 2022; U.S. U.S. patent application Ser. No. 17/076,959, entitled "Ultrasonic Surgical Instrument with a Distally Grounded Acoustic Waveguide," filed on Oct. 22, 2020, published as U.S. Pub. No. 2022/0125464 on Apr. 28, 2022; and/or U.S. U.S. patent application Ser. No. 17/077,098, entitled "Ultrasonic Surgical Instrument with a Multiplanar Articulation Joint," filed on Oct. 22, 2020, published as U.S. Pub. No. 2022/0125467 on Apr. 28, 2022. The disclosure of each of the above-cited U.S. patent applications is incorporated by reference herein in its entirety. Various features of these alternative examples of surgical instruments may be readily incorporated into a surgical robotic system, such as robotic systems (10, 28), such that the invention is not intended to be unnecessarily limited to these particular alternative surgical instruments discussed herein.

A. Overview

Figure 7:
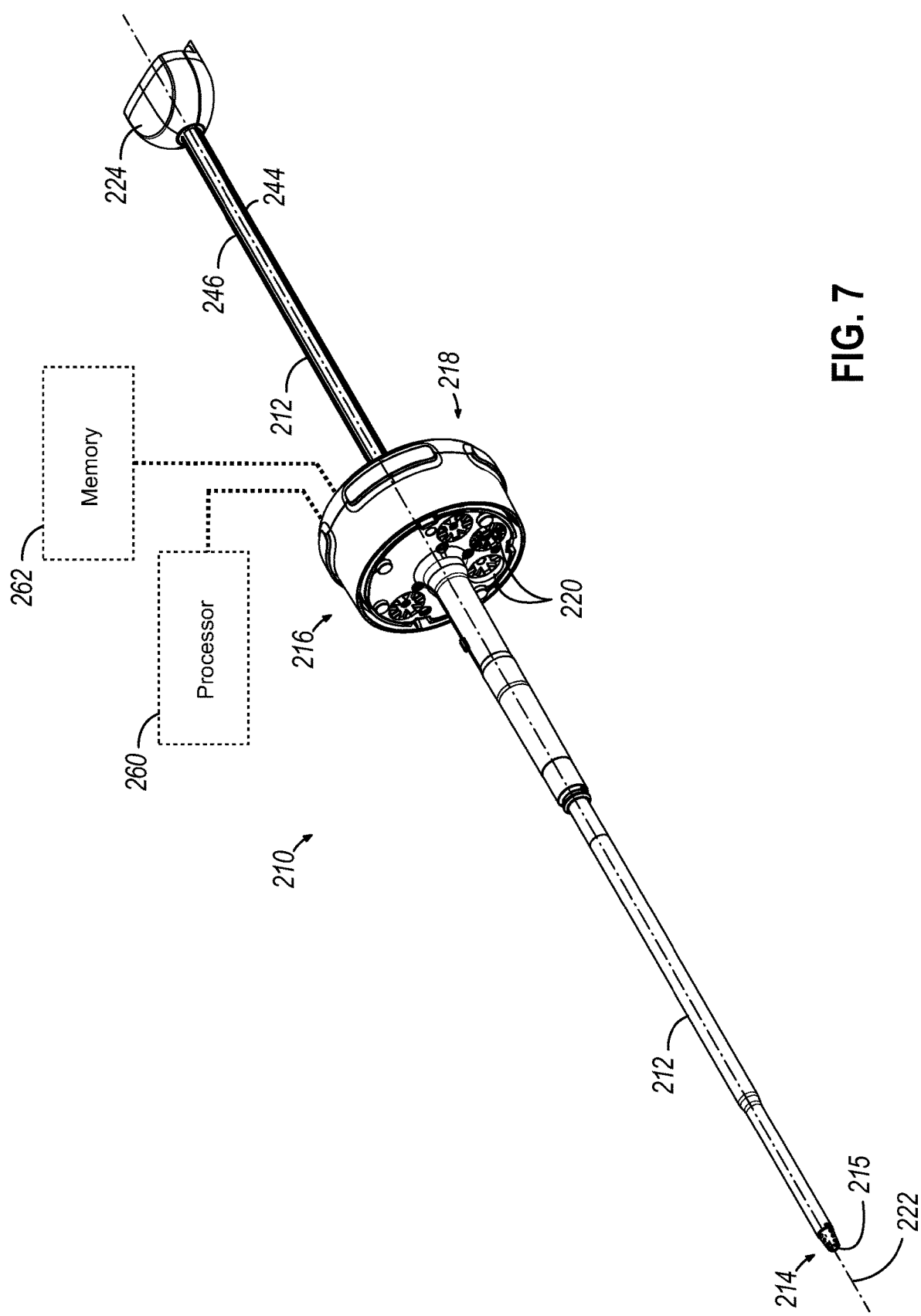
FIG. 7 depicts a perspective view of a second exemplary surgical instrument having a valve adapter for selectively directing suction and irrigation.

FIG. 7 is an exemplary surgical instrument (210) that may incorporate some or all of the principles of the present disclosure. Surgical instrument (210) may be similar in some respects to any of the instruments described above with reference to FIGS. 1-6B and, therefore, may be used in conjunction with a robotic surgical system, such as robotic systems (10, 28) of FIGS. 1-6B. As illustrated, surgical instrument (210) includes an elongated shaft assembly (212) and an end effector (214) arranged at a distal end of shaft assembly (212).

Surgical instrument (210) can have any of a variety of configurations capable of performing one or more surgical functions. In the present example, surgical instrument (210) is more particularly a suction-irrigation surgical instrument (210) with end effector (214) comprising a distal opening (215) configured to apply suction and/or irrigation to a surgical site. Additionally or alternatively, end effector (214) may comprise other types of instruments requiring opposing jaws such as, but not limited to, surgical staplers (e.g., circular and linear staplers), tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), an endoscope (e.g., a camera), an ultrasonic instrument, an RF instrument, or any combination thereof. etc.

Surgical instrument (210) includes an instrument base (216) with an attachment interface (218) operable similar to instrument base (76) and attachment interface (78) described above. Attachment interface (78) further includes one or more drive inputs (220) for coupling with one or more drive outputs, such as drive outputs (68). Shaft assembly (212) extends from a center of instrument base (216) with an axis substantially parallel to the axes of the drive inputs (220) similar to drive inputs (68) as discussed above. Shaft assembly (212) of surgical instrument (14) is thereby configured to rotate about its own longitudinal axis (222) while also longitudinally translating along its axis (222) relative to rotational assembly (70) during use. As will be described in greater detail below, surgical instrument (210) further includes a valve adapter (224). Valve adapter (224) is configured to fluidly couple one or more additional features with end effector (214) via shaft assembly (212), and further to provide operative control of valve adapter (224) by instrument driver (66).

As discussed above, table-based robotic systems (10, 28) (see FIGS. 1-2) have towers (not shown) and/or tables (16, 34) (see FIGS. 1-2) with processing, computing, and/or control capabilities provided at least in part by a processor (260), such as a central processing unit (CPU), and a memory (262). Processor (260) and memory (262) generate, store, and/or communicate data and signals between elements of surgical instrument (210) and towers (not shown) and/or tables (16, 34) (see FIGS. 1-2), such as between one or more sensors as described below, tower (not shown) or table (16) (see FIG. 1). While processor (260) and memory (262) of the present example are depicted as coupled with instrument base (216), it should be understood that processor (260) and memory (262) may instead be coupled with or housed within any portion of surgical instrument (210), towers (not shown) or tables (16, 34) (see FIGS. 1-2).

Figure 8:
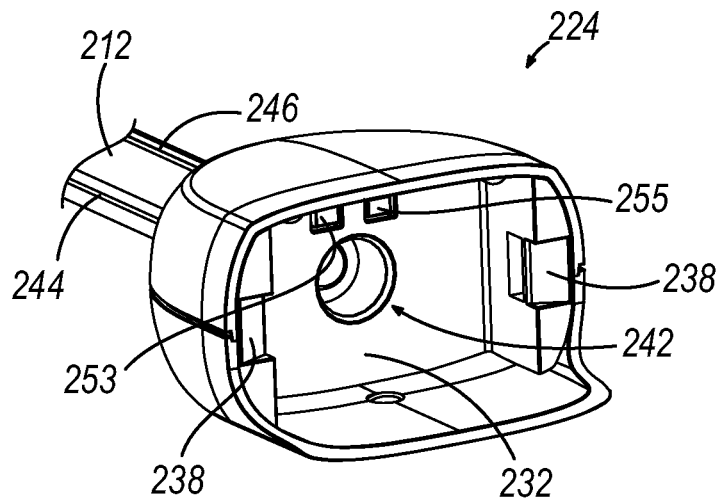
FIG. 8 depicts an enlarged rear perspective view of the valve adapter of FIG. 7.
Figure 9:
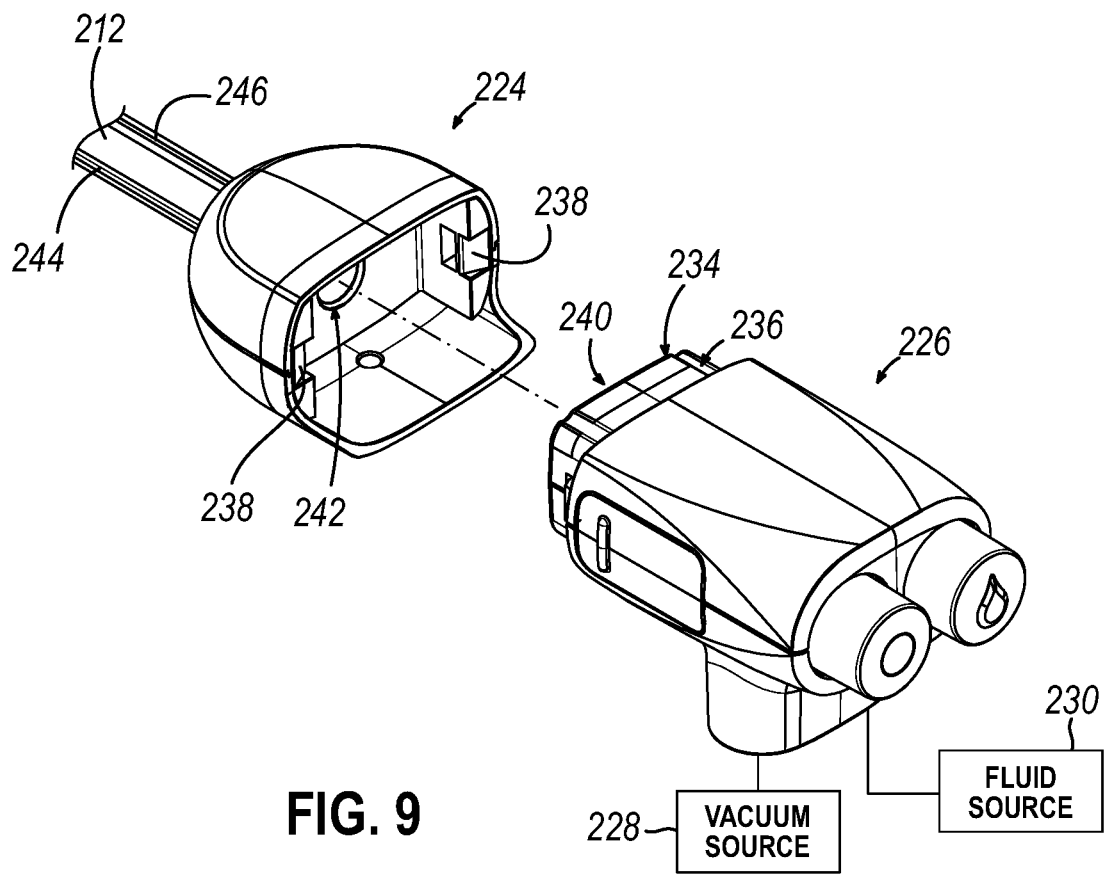
FIG. 9 depicts an enlarged rear perspective view of the valve adapter of FIG. 7 and an example of a spool valve assembly.

Depicted in FIGS. 8-9, valve adapter (224) is configured to fluidly and operably couple with a valve assembly (226) or other similarly operable device to provide one or more fluid connections between valve adapter (224), valve assembly (226), and end effector (214). Accordingly, a proximal face (232) of valve adapter (224) is configured to couple with a distal face (234) of valve assembly (226), using latching connectors (236) and latches (238), such that an outlet (240) of valve assembly (226) fluidly couples with lumen (258) of valve adapter (224) via an input opening (242). The one or more fluid connections may be, for example, a first connection to receive suction from a vacuum (or "suction") source (228) and a second connection to receive fluid from a fluid (or "irrigation") source (230). As will be described in greater detail below, each of vacuum source (228) and fluid source (230) may be coupled with a surface of valve assembly (226), and valve assembly (226) may therefore be operable to selectively couple one or both of vacuum source (228) and fluid source (230) to end effector (214) as directed by instrument driver (66). As such, as fluid or suction from vacuum source (228) and fluid source (230) are activated, any such fluid or suction transmits through a valve chamber, or internal lumen (326), of valve assembly (226), into input opening (242) of valve adapter (224), and flows through inner lumen (258) of valve adapter (224) and into a proximal portion of shaft assembly (212) (see, for example, FIGS. 13A-13C).

Figure 10:
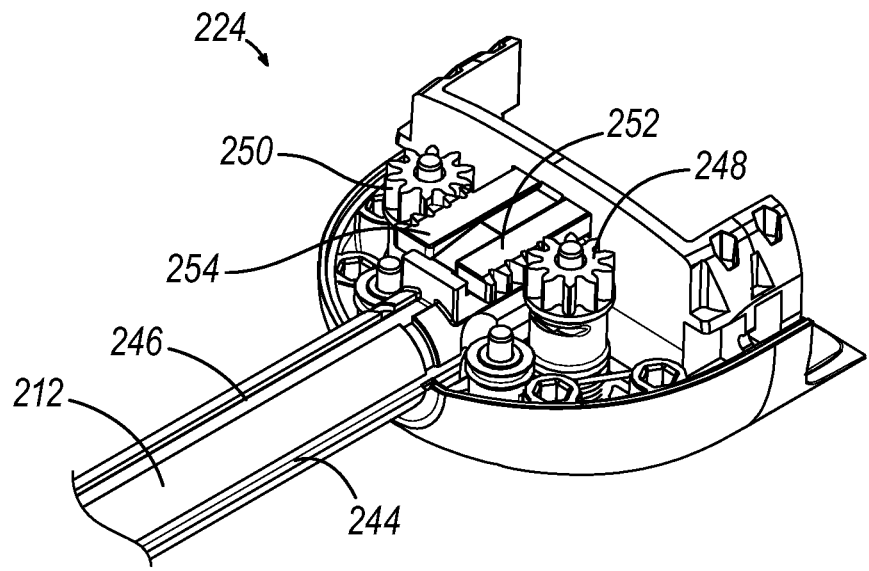
FIG. 10 depicts an enlarged front perspective view of the valve adapter of FIG. 7 having a portion of a housing removed for greater clarity.
Figure 11:
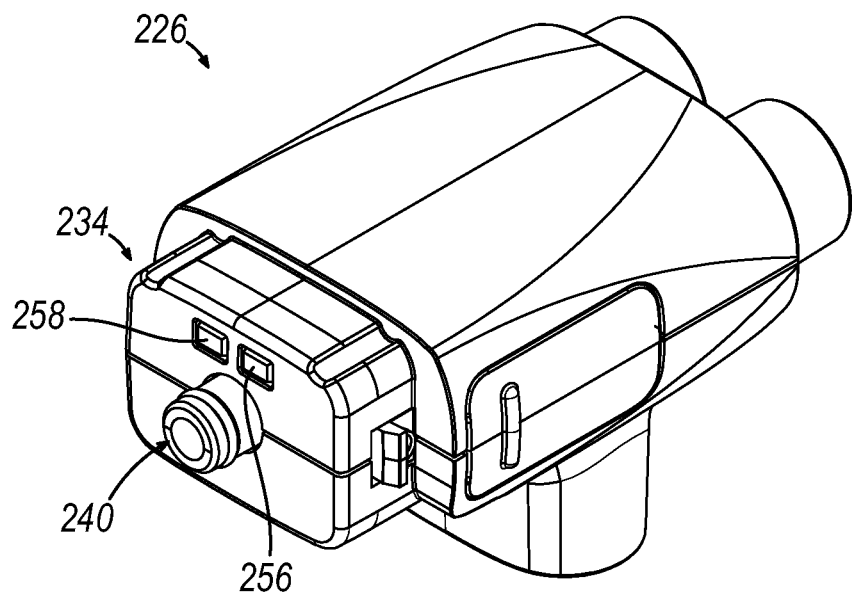
FIG. 11 depicts a front perspective view of the valve assembly of FIG. 9.

To direct the operation of valve assembly (226), one or more pull cables (244, 246) may be operatively coupled between instrument base (216) and valve adapter (224). Depicted in FIG. 10 is valve adapter (224) having a portion of the exterior housing removed for greater clarity. As shown, pull cables (244, 246) may be selectively operable to direct movements of respective pinions (248, 250), which are operably coupled with respective racks (252, 254). As such, translation of pull cables (244, 246) longitudinally along axis (222) converts the longitudinal movements of pull cables (244, 246) to rotational movement of pinions (248, 250), which is again converted back to longitudinal movement of racks (252, 254). As will be described in greater detail below, racks (252, 254) are further configured to provide input operation to valve assembly (226) by extending and retracting longitudinally through openings (253, 255) of valve adapter (see FIG. 8) and into openings (256, 258) of valve assembly (226) (see FIG. 11) of valve assembly (226).

B. Spool Valve Assembly

Figure 12:
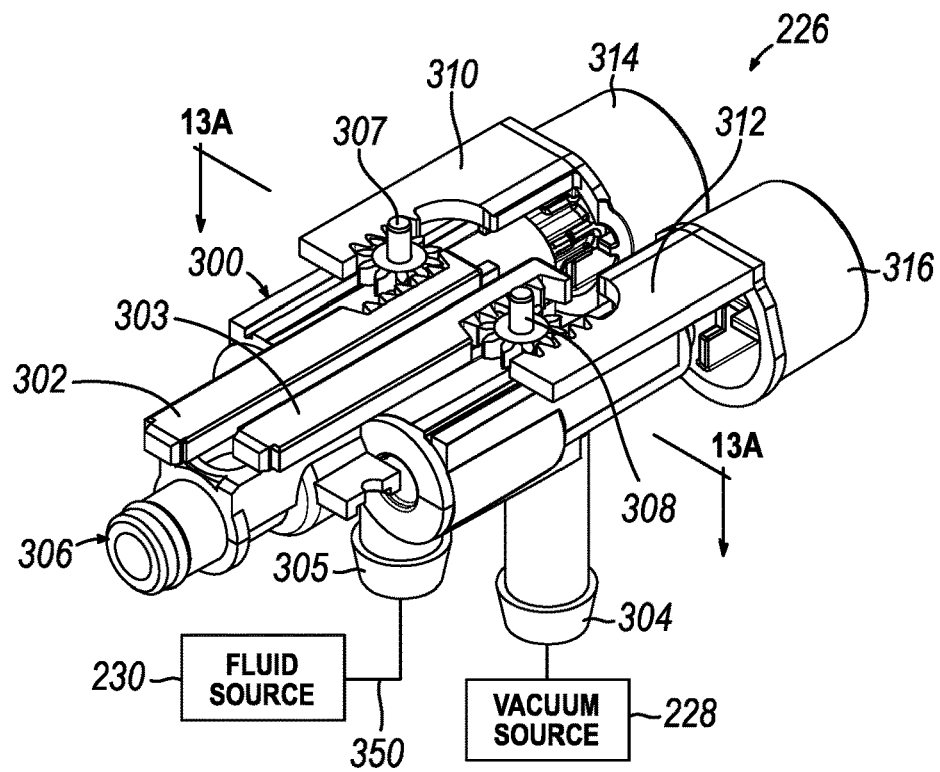
FIG. 12 depicts a front perspective view of the spool valve assembly of FIG. 9 having a housing removed for greater clarity.

In some versions of surgical instrument (210), valve assembly (226) may be configured and operable as a spool valve assembly (226). Depicted in FIG. 12 is spool valve assembly (226) having a portion of the exterior housing body removed for greater clarity. As shown, spool valve assembly (226) includes a valve body (300) and a pair of racks (302, 303) configured to translate longitudinally as directed by racks (252, 254) of valve adapter (224). Valve body (300) has one or more ports, such as vacuum and fluid inlet openings (304, 305), as well as an outlet opening (306). Proximal ends of racks (252, 254) of valve adapter (224) are configured to abut against distal ends of racks (302, 303) of spool valve assembly (226) to translate racks (302, 303) longitudinally, which further acts to rotate pinions (307, 308) of spool valve assembly (226). Each pinion (307, 308) is coupled with one of the valve inputs, specifically, the input from the vacuum source (228) or the input from the fluid source (230). Each pinion (307, 308) is further coupled with a second set of racks (310, 312) which attached to respective fluid and vacuum projections (314, 316). Fluid and vacuum projections (314, 316) are operatively coupled with pinions (307, 308) and configured to translate longitudinally in approximately equal and opposite directions as racks (302, 303) when driven robotically via racks (252, 254). In other words, fluid and vacuum projections (314, 316) generally follow movement of racks (310, 312) and, in this respect, provide a visual indication of valving set for suction or irrigation. In addition or alternatively, robotic operation may be disabled and fluid and vacuum projections (314, 316) may be manually gripped and moved as desired to achieve suction or irrigation.

Accordingly, for example, as first rack (302) translates proximally to rotate first pinion (307), a fluid inlet spool valve plug (318) (see FIGS. 13A-C) from fluid source (230)

is opened to thereby couple fluid source (230) with shaft assembly (212). Fluid projection (314) is further operated to couple with pinion (307) such that it moves distally in correlation with first rack (302) translating proximally as discussed above. Similarly, as second rack (303) translates proximally to rotate second pinion (308), a vacuum inlet spool valve plug (320) (see FIGS. 13A-C) from vacuum source (228) is opened to thereby couple vacuum source (228) with shaft assembly (212). Vacuum projection (316) is further operated to couple with pinion (308) such that it moves distally in correlation with second rack (303) translating proximally as discussed above. In accordance with these features, operation of pull cables (244, 246) by instrument base (216) thereby operates spool valve assembly (226). As shown in the present example, vacuum and fluid inlet spool valve plugs (320, 318) are movably positioned within valve body (300) to a number of predetermined positions described in greater detail below for desired flow of fluid.

Figure 13A:
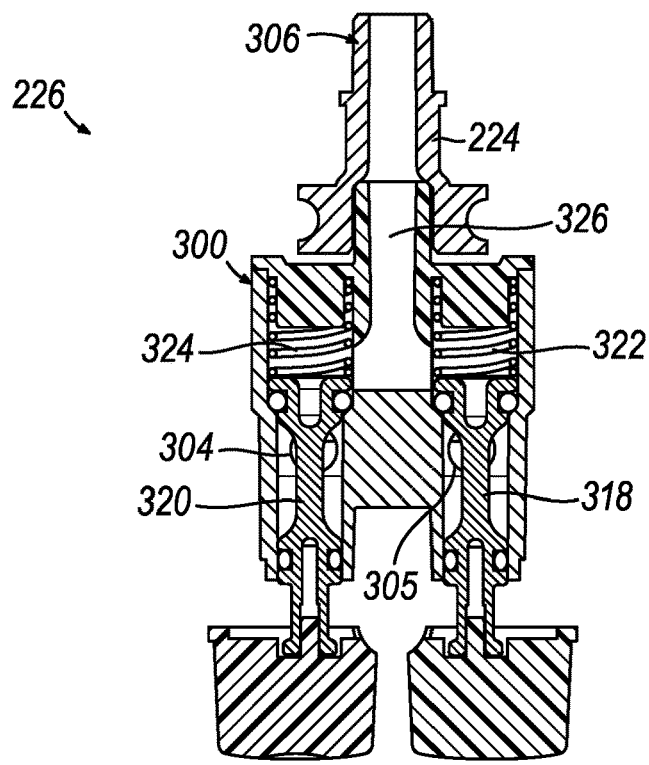
FIG. 13A depicts a cross-sectional view of the spool valve assembly of FIG. 12 taken along section line 13A-13A of FIG. 12 with a vacuum valve in a closed vacuum position and a fluid valve in a closed fluid position such than neither a vacuum inlet nor a fluid inlet is in fluid communication with an outlet.
Figure 13B:
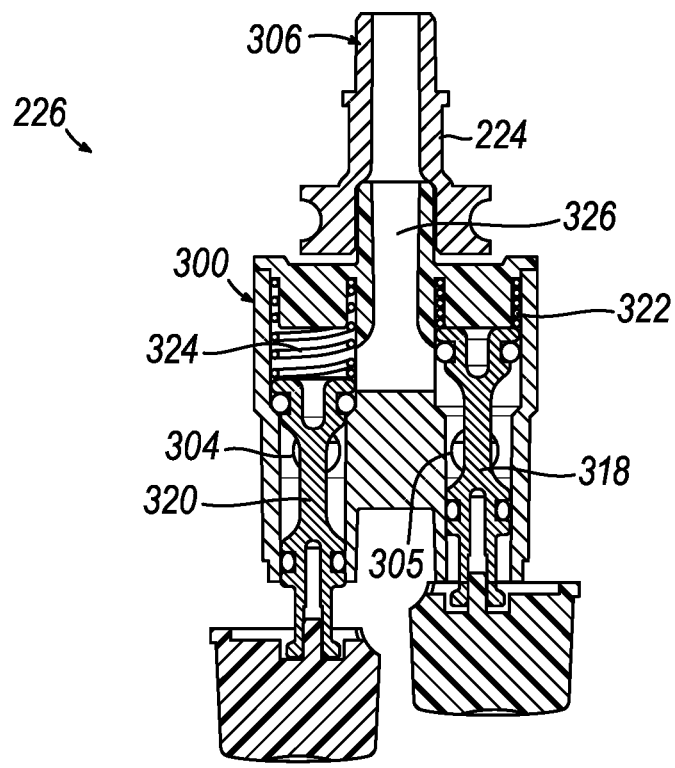
FIG. 13B depicts the cross-sectional view of the spool valve assembly similar to FIG. 13A, but showing the fluid valve in an open fluid position such that the fluid inlet is in fluid communication with the outlet.
Figure 13C:
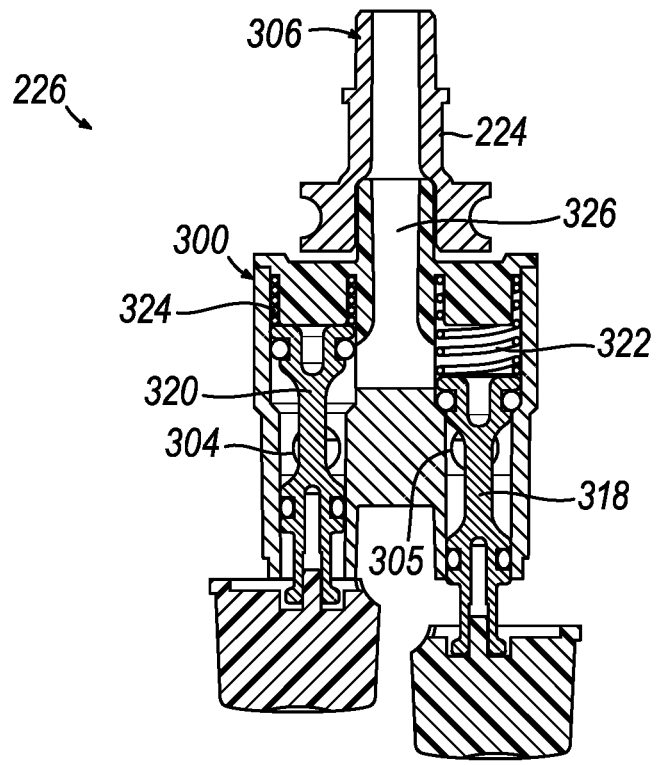
FIG. 13C depicts the cross-sectional view of the spool valve assembly similar to FIG. 13A, but showing the vacuum valve in an open vacuum position such that the vacuum inlet is in fluid communication with the outlet.

Depicted in FIGS. 13A-13C are three different valve position combinations of spool valve assembly (226). Shown in FIG. 13A is spool valve assembly (226) in a first configuration whereby fluid and vacuum inlet valve plugs (318, 320), each respectively being coupled with vacuum source (228) or fluid source (230), are both in a closed position. Springs (322, 324), such as compression springs, act to bias valve plugs (318, 320) and racks (302, 303) in proximal positions until pull cables (244, 246,) selectively pull one or both racks (302, 303) distally using valve adapter (224) as described above. In the closed positions, vacuum source (228) and fluid source (230) are each fluidly decoupled, which may also be referred to herein as fluidly disconnected, from shaft assembly (212) and distal opening (215) of end effector (214). More particularly, outlet opening (306) of spool valve assembly (226) and valve adapter (224) are disconnected from both vacuum and fluid inlet openings (304, 305). Shown in FIG. 13B is spool valve assembly (226) in a second configuration whereby fluid inlet spool valve plug (318) is in an open position to fluidly couple fluid source (230) and fluid inlet opening (305) with outlet opening (306) for fluid communication therethrough while vacuum inlet spool valve plug (320) remains in the closed position. Shown in FIG. 13C is spool valve assembly (226) in a third configuration whereby vacuum inlet spool valve plug (320) is in an open position to (318) fluidly couple vacuum source (228) and vacuum inlet opening (304) with outlet opening (306) for fluid communication therethrough while fluid inlet spool valve plug (318) remains in the closed position.

III. Exemplary Methods of Priming the Suction-Irrigation Surgical Instrument with Fluid In some examples it may be desirable to prime surgical instrument (210) with fluid from fluid source (230) prior to the first use, or in certain circumstances, during an operation. For instance, prior to operating surgical instrument (210), processing, computing, and/or control capabilities stored in one or both of towers (not shown) or tables (16, 34) (see FIGS. 1-2) cycle fluid and vacuum inlet valve plugs (318, 320) to fully open and closed positions to thereby determine these particular fully open and closed positions that may be unique to this particular surgical instrument (210). Such determination may also be referred to herein as "homing" the fluid and vacuum inlet valve plugs (318, 320). Also prior to operating surgical instrument (210), fluid source (230) is fluidly coupled with valve assembly (226) by way of one or more fluid lines (350) (see FIG. 12). Fluid line (350) may be, for example, medical grade tubing that is commonly utilized for administering fluids to a patient. As fluid line (350) is coupled with valve assembly (226) to thereby communicate fluid from fluid source (230), such as irrigation fluid, it may be desirable to prime fluid line (350) to remove any unwanted air bubbles or to cycle a portion of fluid therethrough to pre-fill fluid line (350). More particularly, it may be desirable to prime fluid line (350) without expelling fluid from outlet opening (306) and therefore from end effector (214) via shaft assembly (212). Such priming may thus occur contemporaneously, such as simultaneously, with homing of fluid and vacuum inlet valve plugs (318, 320), such as prior to use of surgical instrument (210) on the patient.

Figure 14:
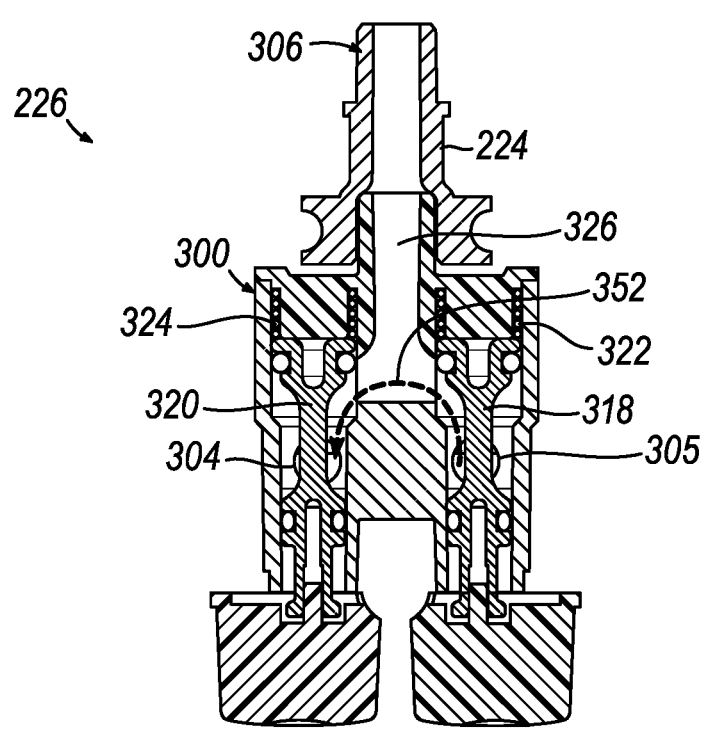
FIG. 14 depicts the cross-sectional view of the spool valve assembly similar to FIG. 13A, but showing the vacuum valve in an open vacuum position and the fluid valve in the open fluid position such that the vacuum inlet is in fluid communication with the fluid inlet.

Accordingly, depicted in FIG. 14 is another valve position combination of spool valve assembly (226). Shown in FIG. 14 is spool valve assembly (226) in a fourth configuration whereby fluid and vacuum inlet valve plugs (318, 320), each respectively being coupled with vacuum source (228) or fluid source (230), are both transitioned to an open position. As described above, springs (322, 324) act to bias valve plugs (318, 320) and racks (302, 303) in proximal positions until pull cables (244, 246,) selectively urge one or both racks (310, 312) distally using valve adapter (224). In the open positions, vacuum source (228) and fluid source (230) are each fluidly coupled, which may also be referred to herein as being in fluid communication, with shaft assembly (212) and distal opening (215) of end effector (214). More particularly, outlet opening (306) of spool valve assembly (226) and valve adapter (224) are in fluid communication with both vacuum and fluid inlet openings (304, 305). Alternatively, valve assembly (226) may be configured to fluidly close distal opening (215) from inner lumen (326) and/or outlet opening (306) while priming surgical instrument (210). It will thus be appreciated that the invention is not intended to be unnecessarily limited to fluidly connecting or disconnecting outlet opening (306) from valve assembly (226) while priming surgical instrument (210).

In the fourth configuration, depicted in FIG. 14, activation of both vacuum source (228) and fluid source (230) results in fluid from fluid source (228) being transferred directly to vacuum source (228) across inner lumen (326) rather than communicating through outlet opening (306) toward shaft assembly (212) and end effector (214). To ensure no fluid from fluid source (230) communicates through outlet opening (306), vacuum source (228) is adequately equipped with a vacuum strength and/or a larger vacuum inlet inner diameter than a fluid inlet inner diameter that is capable of vacuuming all of the fluid from fluid source (230) into a fluid reservoir or drainage outlet (not shown) associated with vacuum source (228). This priming procedure may be accomplished to generally fill fluid line (350) prior to the start of an operation using surgical instrument (210). However, in some instances it may be desirable to repeat this priming procedure during an operation, such as if fluid source (230) encounters an issue and transfers an errant fluid stream which requires further priming (e.g., a fluid stream containing an usually high amount of air bubbles present therein).

Figure 15:
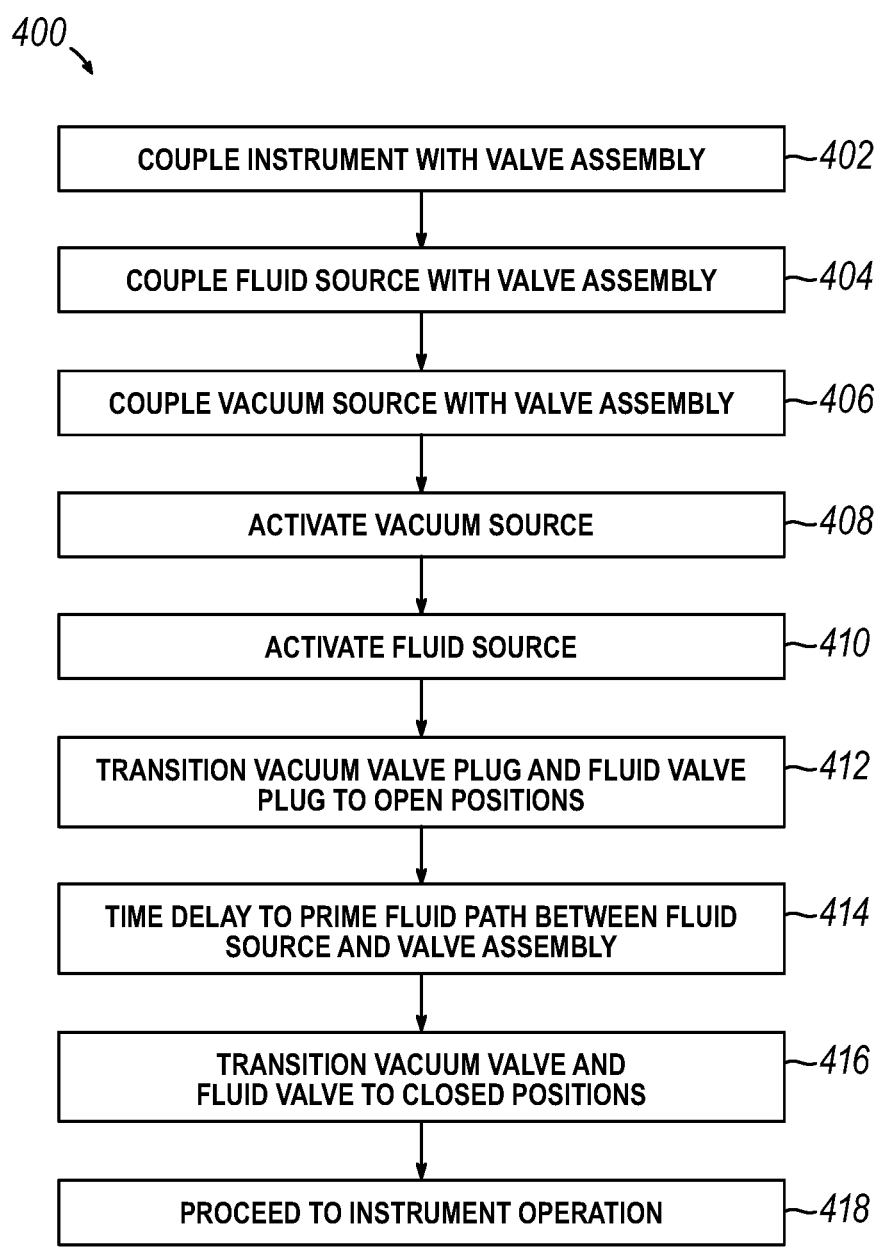
FIG. 15 depicts one exemplary method of priming the surgical instrument of FIG. 7.

Depicted in FIG. 15 is an exemplary method (400) of priming fluid line (350) of surgical instrument (210) prior to an operation. First, at step (402), surgical instrument (210) is coupled with outlet opening (306) of valve assembly (226). Next, at step (404) and at step (406), fluid source (230) and vacuum source (228) are each respectively coupled with valve assembly (226) via vacuum and fluid inlet openings (304, 305). As such, upon operation of valve plug (318) to transition valve plug (318) from a closed position (see FIG. 13A) to an open position (see FIG. 14), such as while homing surgical instrument (210), fluid source (230) is fluidly coupled with inner lumen (326). Further, upon operation of valve plug (320) to transition valve plug (320) from a closed position (see FIG. 13A) to an open position (see FIG. 14), such as while homing surgical instrument (210), vacuum source (228) is also fluidly coupled with inner lumen (326). At steps (408) and (410), vacuum source (228) and fluid source (230) may be activated to provide respective vacuum suction and fluid to vacuum and fluid inlet openings (304, 305).

At step (412), fluid and vacuum inlet valve plugs (318, 320) are transitioned from closed positions to open positions to thereby fluidly communicate the fluid and vacuum with inner lumen (326). In some versions, fluid and vacuum inlet valve plugs (318, 320) are transitioned to open positions simultaneously to prevent any fluid from fluid inlet opening (305) from communicating outward from valve assembly (226) via outlet opening (306). In other versions, vacuum inlet valve plug (320) is transitioned first to ensure that, once fluid inlet valve plug (318) transitions to provide fluid to fluid inlet opening (305), the vacuum suction is already active within inner lumen (326) and ready to vacuum the fluid outward through vacuum inlet (320). Next, at step (414), inlet valve plugs (318, 320) may be held in their respective open positions to allow fluid to transfer outward through vacuum inlet (320) for as long as required to prime fluid line (350). The length of time required to prime the fluid line is variable based on certain factors and circumstances, for example, the size and length of fluid line (350), but may be calculated and/or experimentally determined based on known factors as a predetermined dwell time. One or more predetermined dwell times may be stored on towers (not shown) and/or tables (16, 34) (see FIGS. 1-2). For example, processor (260) and memory storage (262) may include a predetermined dwell time and processor (260) may be configured to selectively move valve assembly (226) to the second configuration for the predetermined dwell time. Inlet valve plugs (318, 320) may thus be held in their respective open positions, whether manually or by automatic operation as directed by processor (260), for the predetermined dwell time to allow fluid to transfer outward through vacuum inlet (320) during step (414).

Next, at step (416), fluid and vacuum inlet valve plugs (318, 320) are transitioned from open positions to closed positions to thereby fluidly decouple the fluid and vacuum from inner lumen (326). In some versions, fluid and vacuum inlet valve plugs (318, 320) are transitioned to closed positions simultaneously to prevent any residual fluid from fluid inlet opening (305) from communicating outward from valve assembly (226) via outlet opening (306). In other versions, fluid inlet valve plug (318) is transitioned first to ensure that all fluid from fluid source (230) is removed via vacuum inlet (320). Thereafter, at step (418), fluid line (350) is primed and surgical instrument (210) may be operated or the surgical operation may otherwise continue.

In one example, after priming of surgical instrument (210), completion of this priming to a primed state is stored to table-based robotic system (28) (see FIG. 1), such as on memory (262) of surgical instrument (210), tower (not shown) and/or table (16) (see FIG. 1). In the event that use of surgical instrument (210) is paused and/or valve assembly (226) removed from valve adapter (224) (see FIG. 7), another aspect of operation on the patient may be performed followed by reconnection and use of surgical instrument (210) with valve assembly (226). Upon use of surgical instrument (210) with valve assembly (226), the primed state is thus known and not repeated as directed by CPU (260) (see FIG. 7) for processing in tower (not shown) and/or table (16) (see FIG. 1).

In some versions, valve assembly (226) may include one or more sensors (not shown) operable to sense whether fluid has transferred into inner lumen (326) from fluid inlet opening (305) to ensure the priming step described with regard to FIGS. 14-15 has been completed prior to operation of surgical instrument (210). As such, sensor (not shown) may be communicatively coupled, whether via sensor wires or wirelessly, to surgical processor (260) and memory (262) of instrument (210), tower (not shown) and/or table (16) (see FIG. 1) of table-based robotic system (10) (see FIG. 1) to alert table-based robotic system (10) and/or an operator that priming method (400) has not yet been completed or that priming method (400) has been completed and thus need not be repeated.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of priming a surgical instrument with a fluid, wherein the surgical instrument includes (a) a shaft assembly including a lumen, and (b) a valve assembly including: (i) a first inlet configured to receive the fluid from a fluid source, (ii) a second inlet configured to receive a suction from a vacuum source, (iii) an outlet in fluid communication with the lumen, (iv) a valve chamber, and (v) at least one valve plug configured to selectively fluidly connect at least two of the outlet, the first inlet, and the second inlet via the valve chamber, the method comprising: (a) activating the fluid source to provide the fluid to the first inlet; (b) activating the vacuum source to provide the suction to the second inlet; (c) transitioning the at least one valve plug from a first position to a second position, wherein: (i) in the first position the fluid source and the vacuum source are each fluidly decoupled from the valve chamber, and (ii) in the second position the fluid source and the vacuum source are each in fluid communication with the valve chamber; and (d) transferring, via the suction, a first portion of the fluid from the first inlet toward the vacuum source through the second inlet thereby priming the surgical instrument.

Example 2

The method of Example 1, wherein transitioning the at least one valve plug from a first position to a second position includes simultaneously opening the first inlet and the second inlet.

Example 3

The method of any of Examples 1-2, further comprising: after transferring a first portion of the fluid from the first inlet toward the vacuum source, transitioning the at least one valve plug from the second position to the first position.

Example 4

The method of Example 3, wherein transitioning the at least one valve plug from the second position to first position includes simultaneously closing the first inlet and the second inlet.

Example 5

The method of any of Examples 1-4, wherein the at least one valve plug includes: (a) a fluid valve plug selectively operable to open and close the first inlet; and (b) a vacuum valve plug selectively operable to open and close the second inlet.

Example 6

The method of Example 5, wherein the fluid valve plug and the vacuum valve plug are respectively biased toward a fluid closed position and a vacuum closed position, wherein in the fluid and vacuum closed positions the fluid source and the vacuum source are each fluidly decoupled from the valve chamber.

Example 7

The method of Example 6, wherein the fluid valve plug and the vacuum valve plug are each biased toward the fluid and vacuum closed positions by one or more compression springs.

Example 8

The method of any of Examples 1-7, further comprising: transferring, via the suction, a first portion of the fluid from the first inlet toward the vacuum source through the second inlet for a predetermined dwell time thereby priming the surgical instrument.

Example 9

The method of any of Examples 1-8, wherein the surgical instrument further includes an end effector distally extending from the shaft assembly, wherein the end effector includes an opening fluidly connected to the lumen.

Example 10

The method of any of Examples 1-9, wherein the surgical instrument further includes a fluid supply line for fluidly coupling the fluid source with the first inlet, wherein in the second position the portion of the fluid is transferred toward the vacuum source to prime the fluid supply line.

Example 11

The method of Example 10, wherein in the second position the vacuum source suctions through the second inlet all of the fluid that passes through the first inlet.

Example 12

The method of any of Examples 1-11, further comprising: after transferring a first portion of the fluid from the first inlet toward the vacuum source, transitioning the at least one valve plug from the second position to first position; and transitioning the at least one valve plug from the first position to a third position, wherein in the third position the fluid source is fluidly coupled with the valve chamber and the vacuum source is fluidly decoupled from the valve chamber.

Example 13

The method of any of Examples 1-12, further comprising: after transferring a first portion of the fluid from the first inlet toward the vacuum source, transitioning the at least one valve plug from the second position to first position; and transitioning the at least one valve plug from the first position to a fourth position, wherein in the fourth position the fluid source is fluidly decoupled from the valve chamber and the vacuum source is fluidly coupled with the valve chamber.

Example 14

The method of any of Examples 1-13, wherein the surgical instrument further includes a rotary drive member operatively connected to a linear actuator and configured to be rotatably driven about a drive axis via the linear actuator, wherein the rotary drive member is driven by at least one robotic arm movable relative to a patient support.

Example 15

The method of any of Examples 1-14, wherein the shaft assembly extends along a longitudinal axis and further includes a linear actuator configured to selectively translate relative to the longitudinal axis, wherein the linear actuator is operatively connected to the rotary drive member and configured to selectively direct rotation of the rotary drive member.

Example 16

A robotic surgical system, comprising: (a) a shaft assembly including a lumen; (b) a valve assembly including: (i) a first inlet configured to couple with a fluid supply line to receive a fluid from a fluid source, (ii) a second inlet configured to receive a suction from a vacuum source, (iii) an outlet in fluid communication with the lumen, (iv) a valve chamber, (v) a fluid valve plug configured to selectively fluidly communicate the fluid source with the valve chamber via the first inlet, and (vi) a vacuum valve plug configured to selectively fluidly communicate the vacuum source with the valve chamber via the second inlet; wherein the valve assembly is configured to operate in a first configuration and a second configuration, wherein: (i) in the first configuration the fluid valve plug and the vacuum valve plug are both closed thereby configured to fluidly decouple the fluid source and the vacuum source from the valve chamber, and (ii) in the second configuration the fluid valve plug and the vacuum valve plug are both open thereby configured to fluidly couple the fluid source and the vacuum source with the valve chamber such that the vacuum source suctions through the second inlet all of the fluid that passes through the inlet port.

Example 17

The surgical apparatus of Example 16, further comprising a processor and a memory storage including a predetermined dwell time, wherein the processor is configured to selectively move the valve assembly to the second configuration for the predetermined dwell time.

Example 18

The surgical apparatus of any of Examples 16-17, wherein the fluid valve plug and the vacuum valve plug are operable to open and close simultaneously.

Example 19

The surgical apparatus of any of Examples 16-18, wherein the valve assembly is configured to operate in a third configuration and a fourth configuration, wherein: (a) in the third position the first inlet is fluidly coupled with the valve chamber and the second inlet is fluidly decoupled from the valve chamber, and (b) in the fourth position the first inlet is fluidly decoupled from the valve chamber and the second inlet is fluidly coupled with the valve chamber.

Example 20

A method of priming a surgical instrument with a fluid, wherein the surgical instrument includes (a) a shaft assembly including a lumen, and (b) a valve assembly including (i) a first inlet configured to receive the fluid from a fluid source, (ii) a second inlet configured to receive a suction from a vacuum source, (iii) an outlet in fluid communication with the lumen, (iv) a valve chamber, (v) a fluid valve plug selectively operable to open and close the first inlet, and (vi) a vacuum valve plug selectively operable to open and close the second inlet, the method comprising: (a) activating the fluid source to provide the fluid to the first inlet; (b) activating the vacuum source to provide the suction to the second inlet; (c) transitioning the vacuum valve plug from a first vacuum valve position to a second vacuum valve position, wherein: (i) in the first vacuum valve position the vacuum source is fluidly decoupled from the valve chamber, and (ii) in the second vacuum valve position the vacuum source is in fluid communication with the valve chamber; (d) transitioning the fluid valve plug from a first fluid valve position to a second fluid valve position, wherein: (i) in the first fluid valve position the fluid source is fluidly decoupled from the valve chamber, and (ii) in the second fluid valve position the fluid source is in fluid communication with the valve chamber; (d) transferring, via the suction, the fluid directly from the first inlet toward the vacuum source through the second inlet thereby priming the surgical instrument.

VI. Miscellaneous

Any one or more of the teaching, expressions, embodiments, examples, etc. described herein may be combined with any one or more of the teachings, expressions, embodiments, examples, etc. described in U.S. Pat. App. No. 17/345,119, entitled "Suction and Irrigation Valve and Method of Priming Same in a Robotic Surgical System," filed on Jun. 11, 2021, published as U.S. Pub. No. 2022/0395626 on Dec. 15, 2022, and incorporated by reference in its entirety herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, mate-

I claim:

1. A method of priming a surgical instrument with a fluid, wherein the surgical instrument includes (a) a shaft assembly including a lumen, and (b) a valve assembly including: (i) a first inlet configured to receive the fluid from a fluid source, (ii) a second inlet configured to receive a suction from a vacuum source, (iii) an outlet in fluid communication with the lumen, (iv) a valve chamber, and (v) at least one valve plug configured to selectively fluidly connect at least two of the outlet, the first inlet, and the second inlet via the valve chamber, the method comprising:
   (a) activating the fluid source to provide the fluid to the first inlet;
   (b) activating the vacuum source to provide the suction to the second inlet;
   (c) transitioning the at least one valve plug from a first position to a second position, wherein:
      (i) in the first position the fluid source and the vacuum source are each fluidly decoupled from the valve chamber, and
      (ii) in the second position the fluid source and the vacuum source are each in fluid communication with the valve chamber; and
   (d) transferring, via the suction, a first portion of the fluid from the first inlet toward the vacuum source through the second inlet thereby priming the surgical instrument.

2. The method of claim 1, wherein transitioning the at least one valve plug from a first position to a second position includes simultaneously opening the first inlet and the second inlet.

3. The method of claim 1, further comprising:
   after transferring a first portion of the fluid from the first inlet toward the vacuum source, transitioning the at least one valve plug from the second position to the first position.

4. The method of claim 3, wherein transitioning the at least one valve plug from the second position to first position includes simultaneously closing the first inlet and the second inlet.

5. The method of claim 1, wherein the at least one valve plug includes:
   (a) a fluid valve plug selectively operable to open and close the first inlet; and
   (b) a vacuum valve plug selectively operable to open and close the second inlet.

6. The method of claim 5, wherein the fluid valve plug and the vacuum valve plug are respectively biased toward a fluid closed position and a vacuum closed position, wherein in the fluid and vacuum closed positions the fluid source and the vacuum source are each fluidly decoupled from the valve chamber.

7. The method of claim 6, wherein the fluid valve plug and the vacuum valve plug are each biased toward the fluid and vacuum closed positions by one or more compression springs.

8. The method of claim 1, further comprising: transferring, via the suction, a first portion of the fluid from the first inlet toward the vacuum source through the second inlet for a predetermined dwell time thereby priming the surgical instrument.

9. The method of claim 1, wherein the surgical instrument further includes an end effector distally extending from the shaft assembly, wherein the end effector includes an opening fluidly connected to the lumen.

10. The method of claim 1, wherein the surgical instrument further includes a fluid supply line for fluidly coupling the fluid source with the first inlet, wherein in the second position the portion of the fluid is transferred toward the vacuum source to prime the fluid supply line.

11. The method of claim 10, wherein in the second position the vacuum source suctions through the second inlet all of the fluid that passes through the first inlet.

12. The method of claim 1, further comprising:
   after transferring a first portion of the fluid from the first inlet toward the vacuum source, transitioning the at least one valve plug from the second position to first position; and
   transitioning the at least one valve plug from the first position to a third position, wherein in the third position the fluid source is fluidly coupled with the valve chamber and the vacuum source is fluidly decoupled from the valve chamber.

13. The method of claim 1, further comprising:
   after transferring a first portion of the fluid from the first inlet toward the vacuum source, transitioning the at least one valve plug from the second position to first position; and
   transitioning the at least one valve plug from the first position to a fourth position, wherein in the fourth position the fluid source is fluidly decoupled from the valve chamber and the vacuum source is fluidly coupled with the valve chamber.

14. The method of claim 1, wherein the surgical instrument further includes a rotary drive member operatively connected to a linear actuator and configured to be rotatably driven about a drive axis via the linear actuator, wherein the rotary drive member is driven by at least one robotic arm movable relative to a patient support.

15. The method of claim 1, wherein the shaft assembly extends along a longitudinal axis and further includes a linear actuator configured to selectively translate relative to the longitudinal axis, wherein the linear actuator is operatively connected to the rotary drive member and configured to selectively direct rotation of the rotary drive member.

16. A method of priming a surgical instrument with a fluid, wherein the surgical instrument includes (a) a shaft assembly including a lumen, and (b) a valve assembly including (i) a first inlet configured to receive the fluid from a fluid source, (ii) a second inlet configured to receive a suction from a vacuum source, (iii) an outlet in fluid communication with the lumen, (iv) a valve chamber, (v) a fluid valve plug selectively operable to open and close the first inlet, and (vi) a vacuum valve plug selectively operable to open and close the second inlet, the method comprising:
   (a) activating the fluid source to provide the fluid to the first inlet;
   (b) activating the vacuum source to provide the suction to the second inlet;
   (c) transitioning the vacuum valve plug from a first vacuum valve position to a second vacuum valve position, wherein:
      (i) in the first vacuum valve position the vacuum source is fluidly decoupled from the valve chamber, and
      (ii) in the second vacuum valve position the vacuum source is in fluid communication with the valve chamber;

(d) transitioning the fluid valve plug from a first fluid valve position to a second fluid valve position, wherein:
  (i) in the first fluid valve position the fluid source is fluidly decoupled from the valve chamber, and
  (ii) in the second fluid valve position the fluid source is in fluid communication with the valve chamber;
(d) transferring, via the suction, the fluid directly from the first inlet toward the vacuum source through the second inlet thereby priming the surgical instrument.

\* \* \* \* \*